United States Patent [19]
Hwang et al.

[11] Patent Number: 5,706,819
[45] Date of Patent: Jan. 13, 1998

[54] ULTRASONIC DIAGNOSTIC IMAGING WITH HARMONIC CONTRAST AGENTS

[75] Inventors: Juin-Jet Hwang, Mercer Island, Wash.; David Hope Simpson, Toronto, Canada

[73] Assignee: Advanced Technology Laboratories, Inc., Bothell, Wash.

[21] Appl. No.: 728,318

[22] Filed: Oct. 9, 1996

[51] Int. Cl.$^6$ .................................................. A61B 8/00
[52] U.S. Cl. .................................................. 128/662.02
[58] Field of Search .................. 128/660.01, 662.02; 424/9.5, 9.51, 9.52; 367/7

[56] References Cited

U.S. PATENT DOCUMENTS

| | | | |
|---|---|---|---|
| 4,572,203 | 2/1986 | Feinstein | 128/661 |
| 5,135,000 | 8/1992 | Akselrod et al. | 128/662.02 |
| 5,224,481 | 7/1993 | Ishihara et al. | 128/660.07 |
| 5,233,993 | 8/1993 | Kawano | 128/660.07 |
| 5,241,473 | 8/1993 | Ishihara et al. | 364/413.25 |
| 5,255,683 | 10/1993 | Monaghan | 128/662.02 |
| 5,302,372 | 4/1994 | Lin et al. | 128/662.02 |
| 5,410,516 | 4/1995 | Uhlendorf et al. | 367/7 |
| 5,453,575 | 9/1995 | O'Donnell et al. | 128/661.01 X |
| 5,456,257 | 10/1995 | Johnson et al. | 128/662.02 |

OTHER PUBLICATIONS

Charles C. Church, "The effect of an elastic solid surface layer on the radial pulsation of gas bubbles," JASA v. 97, No. 3, Mar. 1995, 1510–21.

D.L. Miller, "Ultrasonic detection of resonant cavitation bubbles in a flow tube by their second–harmonic emissions," Ultrasonics, Sep. 1981, pp. 217–224.

*Primary Examiner*—Francis Jaworski
*Attorney, Agent, or Firm*—W. Brinton Yorks, Jr.

[57] ABSTRACT

Apparatus and methods are disclosed for the detection and imaging of ultrasonic harmonic contrast agents. The harmonic echo effect is detected through alternate polarity acquisition of harmonic contrast agent effects, which provides the benefits of suppressing the harmonic components of the transmitted signal while eliminating clutter.

4 Claims, 5 Drawing Sheets

ULTRASONIC DIAGNOSTIC IMAGING WITH HARMONIC CONTRAST AGENTS

This invention relates to ultrasonic diagnosis and imaging of the body with ultrasonic contrast agents and, in particular, to new methods and apparatus for ultrasonically detecting and imaging with contrast agents.

Ultrasonic diagnostic imaging systems are capable of imaging and measuring the physiology within the body in a completely noninvasive manner. Ultrasonic waves are transmitted into the body from the surface of the skin and are reflected from tissue and cells within the body. The reflected echoes are received by an ultrasonic transducer and processed to produce an image or measurement of blood flow. Diagnosis is thereby possible with no intervention into the body of the patient.

However materials known as ultrasonic contrast agents can be introduced into the body to enhance ultrasonic diagnosis. Contrast agents are substances which will strongly interact with ultrasonic waves, returning echoes which may be clearly distinguished from those returned by blood and tissue. One class of substances which has been found to be especially useful as an ultrasonic contrast agent is gases, in the form of tiny bubbles called microbubbles. Microbubbles present a significant acoustic impedance mismatch in comparison to tissue and fluids, and nonlinear behavior in certain acoustic fields which is readily detectable through special ultrasonic processing. In order to infuse bubbles into the body so that they will survive passage through the pulmonary system and circulate throughout the vascular system, gases have been stabilized in solutions in the form of tiny microbubbles. Microbubble contrast agents are useful for imaging the body's vascular system, for instance, as the contrast agent can be injected into the bloodstream and will pass through the veins and arteries of the body with the blood supply until filtered from the blood stream in the lungs, kidneys and liver.

One property of microbubble contrast agents currently under investigation is harmonic response. These harmonic contrast agents exhibit significant, detectable responses at frequencies which are harmonics of the transmitted ultrasonic frequency. This property is useful for clutter rejection of the received signals. When the transmitted frequency band is used as the received frequency band, echoes will be returned from the microbubbles, but also from surrounding tissue, the latter comprising clutter in the received echo signals. But with harmonic contrast agents, reception occurs at harmonic frequencies, where fundamental band clutter from tissue is ignored. Since tissue generally reflects very minimal harmonic components, the received harmonic band enables the microbubble echoes to be received with a high signal to noise ratio.

In accordance with the principles of present invention, a technique is provided for the detection and imaging of harmonic ultrasonic contrast agents. The harmonic contrast agent is insonified by alternate polarity transmitted pulses, and the echo signals received from the transmitted pulses are combined. The result is a suppression of harmonic components of the transmitted ultrasonic waves and the elimination of clutter.

Figure 1:
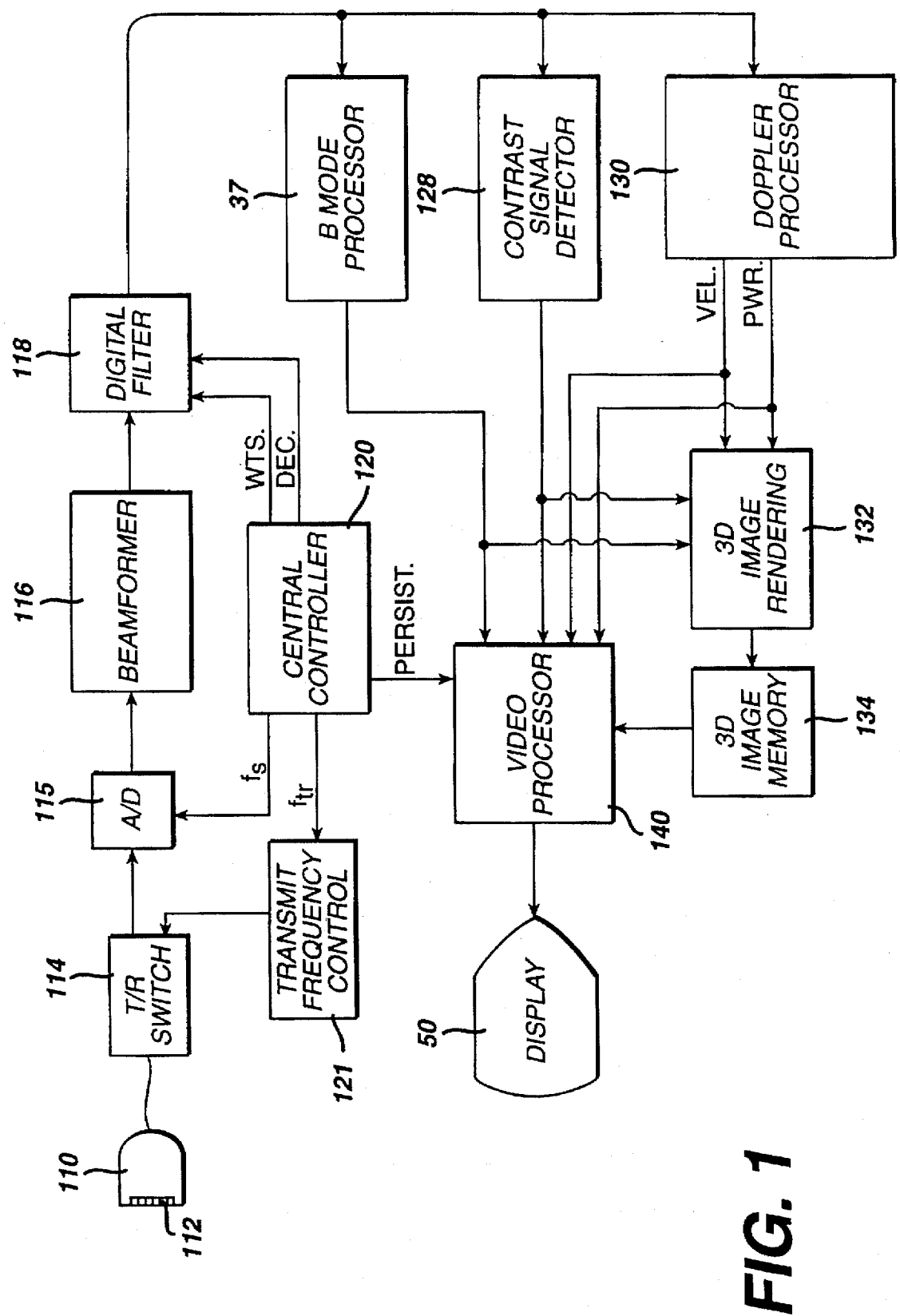
FIG. 1 illustrates in block diagram form apparatus constructed in accordance with the present invention which provides performance advantages for harmonic contrast agent detection.
Figure 2:
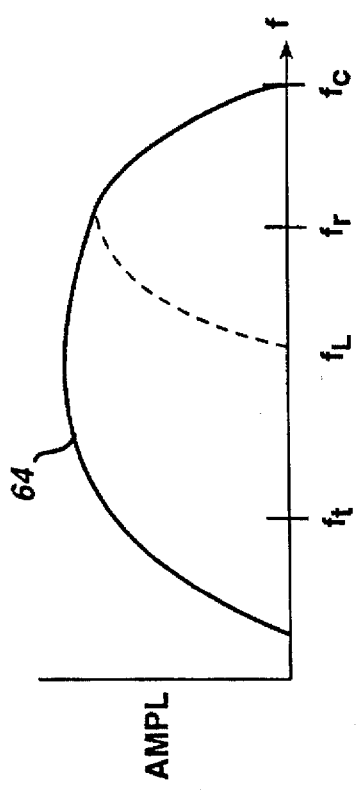
FIGS. 2 and 3 illustrate passband characteristics used to explain the performance of the embodiment of FIG. 1.
Figure 3:
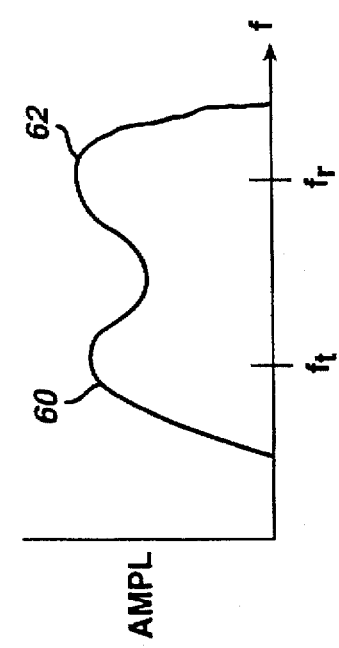

Referring to FIG. 1, an ultrasonic diagnostic system for use with harmonic contrast agents in accordance with the present invention is shown in block diagram form. In this system an array transducer 112 of a probe 110 transmits ultrasonic energy and receives echoes returned in response to this transmission. The response characteristic of the transducer can exhibit two passbands, one around the central transmit frequency and another about the center of the received passband. For imaging harmonic contrast agents, a broadband transducer having a passband encompassing both the transmit and receive passbands is preferred. The transducer may be manufactured and tuned to exhibit a response characteristic as shown in FIG. 2, in which the lower hump 60 of the response characteristic is centered about the center transmit frequency $f_t$, and the upper hump 62 is centered about the center frequency $f_r$ of the response passband. The transducer response characteristic of FIG. 3 is preferred, however, as the single dominant characteristic 64 allows the probe to be suitable for both harmonic contrast imaging and imaging without harmonic contrast agents. The characteristic 64 encompasses the central transmit frequency $f_t$, and also the harmonic receive passband bounded between frequencies $f_L$ and $f_c$, and centered about frequency $f_r$. A typical harmonic contrast agent can have a response such that transmission about a central transmit frequency of 1.7 MHz will result in harmonic returning echo signals about a frequency of 3.4 MHz. A bandwidth characteristic 64 of approximately 2 MHz would be suitable for these harmonic frequencies.

In FIG. 1 a central controller 120 provides a control signal $f_{tr}$ to a transmit frequency control circuit or pulser 121 to control the center frequency and time of transmission of the transmitted ultrasonic energy. The transmit frequency control circuit pulses the elements of the transducer array 112 by means of a transmit/receive switch 114.

Echoes received by the transducer array 112 are coupled through the T/R switch 114 and digitized by analog to digital converters 115. The sampling frequency $f_s$ of the A/D converters 115 is controlled by the central controller. The desired sampling rate dictated by sampling theory is at least twice the highest frequency $f_c$ of the received passband and, for the preceding exemplary frequencies, might be on the order of at least 8 MHz. Sampling rates higher than the minimum requirement are also desirable.

The echo signal samples from the individual transducer elements are delayed and summed by a beamformer 116 to form coherent echo signals. The digital coherent echo signals are then filtered by a digital filter 118. In this embodiment, the transmit frequency $f_{tr}$ is not tied to the receiver, and hence the receiver is free to receive a band of frequencies which is separate from the transmitted band. The digital filter 118 bandpass filters the signals in the passband bounded by frequencies $f_L$ and $f_c$ in FIG. 3, and can also shift the frequency band to a lower or baseband frequency range. The digital filter could be a filter with a 1 MHz passband and a center frequency of 3.4 MHz in the above example. A preferred digital filter is a parallel arrangement of serially coupled multipliers and accumulators. This arrangement is controlled by the central controller 120, which provides multiplier weights and decimation control which control the characteristics of the digital filter. Preferably the arrangement is controlled to operate as a finite impulse response (FIR) filter, and performs both filtering and decimation.

Filtered echo signals from tissue, generally filtered by a passband centered about or demodulated from the transmit frequency, are coupled to a B mode processor 37 for conventional B mode processing. Filtered echo signals of the harmonic contrast agent passband are coupled to a contrast signal detector 128 which performs pulse to pulse summation or integration of temporally discrete echoes from a given spatial location, amplitude or envelope detects the combined signals. Simple two pulse summation of the form $P_1+P_2$ may be employed where $P_1$ represents the echoes received following one pulse and $P_2$ represents the echoes received following another pulse. The combination of echoes from consecutive pulses may, if desired, be performed before the digital filter 118 rather than after, the decision being a matter of choice of system design.

The filtered echo signals from the digital filter 118 are also coupled to a Doppler processor 130 for conventional Doppler processing to produce velocity and power Doppler signals. The outputs of these processors are coupled to a 3D image rendering processor 132 for the rendering of three dimensional images, which are stored in a 3D image memory 134. Three dimensional rendering may be performed as described in U.S. patent application Ser. No. 08/638,710, and in U.S. Pat. Nos. 5,474,073 and 5,485,842, the latter two patents illustrating three dimensional power Doppler ultrasonic imaging techniques. The signals from the contrast signal detector 128, the processors 37 and 130, and the three dimensional image signals are coupled to a video processor 140 where they may be selected for display on an image display 50 as dictated by user selection. The video processor preferably includes persistence processing, whereby momentary intensity peaks of detected contrast agents can be sustained in the image. One technique for providing persistence is through frame averaging, whereby new image frames are combined with previous frame information on a spatial basis. The combination can be done by weighting the contributions of the old and new frame information and the frame information can be combined in a recursive manner; that is, old frame information is fed back for combining with new frame information. A preferred persistence technique is the fast attack, slow decay technique described in U.S. Pat. No. 5,215,094, which can be applied to both Doppler and contrast agent images.

Figure 4A:
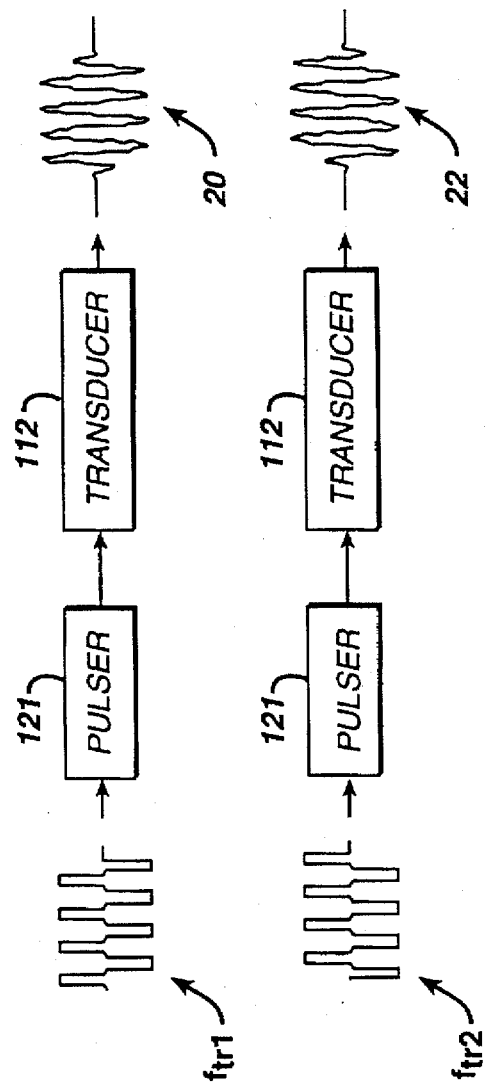
FIGS. 4a and 4b illustrates the alternate polarity pulsing of harmonic contrast agents.
Figure 4B:
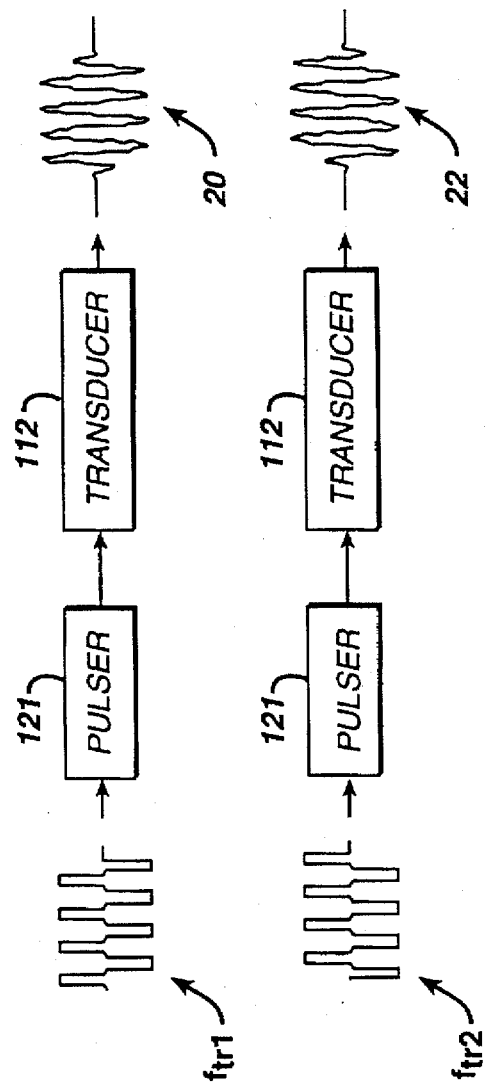

The apparatus of FIG. 1 performs alternate polarity pulse transmission as illustrated in FIGS. 4a and 4b. In the first transmission of FIG. 4a, the central controller 120 provides a first polarity control signal $f_{\pi 1}$ to the pulser 121, which drives the transducer elements 112 to transmit a first polarity pulse 20. For the second transmission of FIG. 4b, the central controller 120 provides a second polarity control signal $f_{\pi 2}$ to the pulser 121, which drives the transducer elements 112 to transmit a second polarity pulse 22.

Figure 5A:
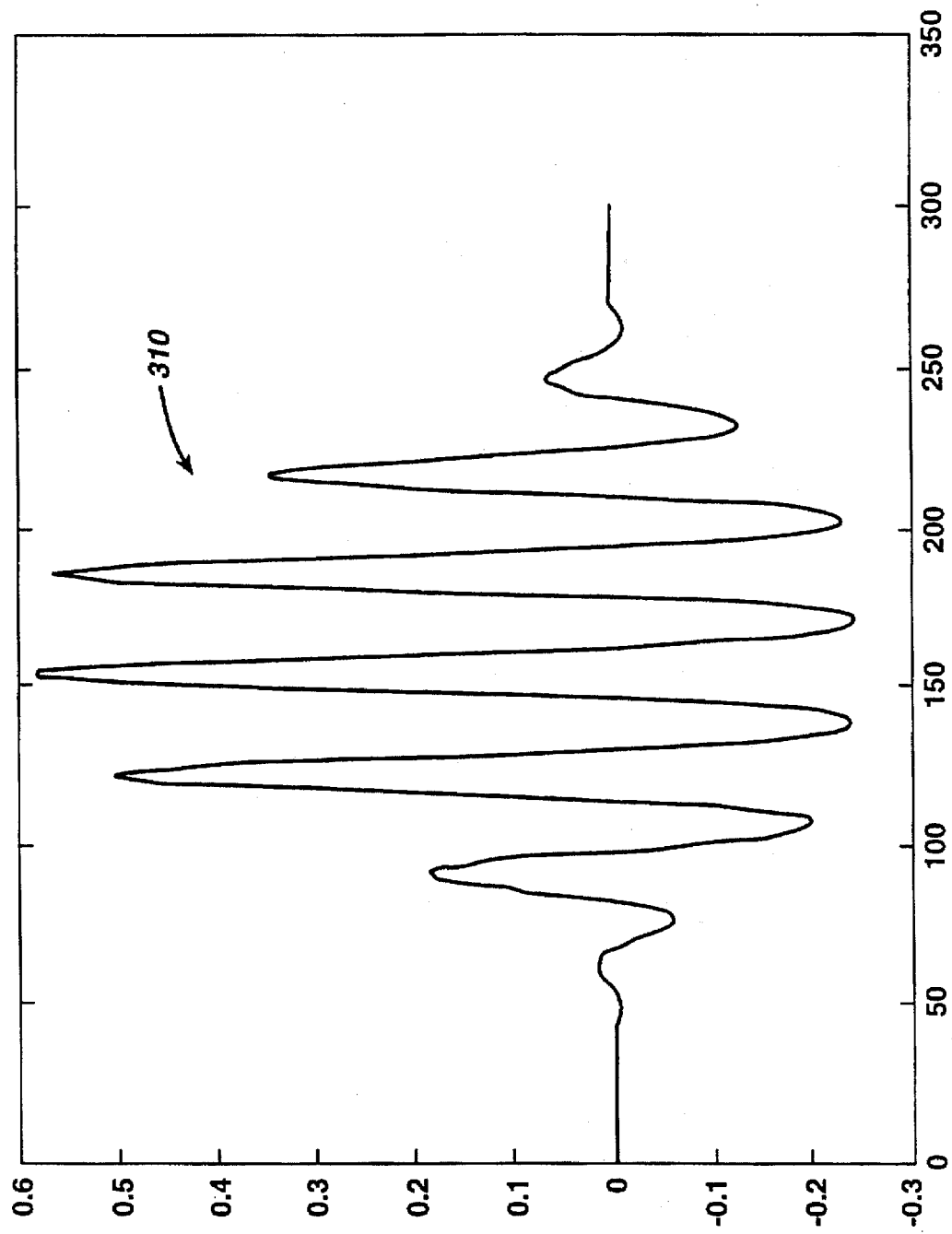
FIGS. 5a–5c illustrate nonlinear response waveforms produced by alternate polarity acquisition of contrast agent echoes.
Figure 5B:
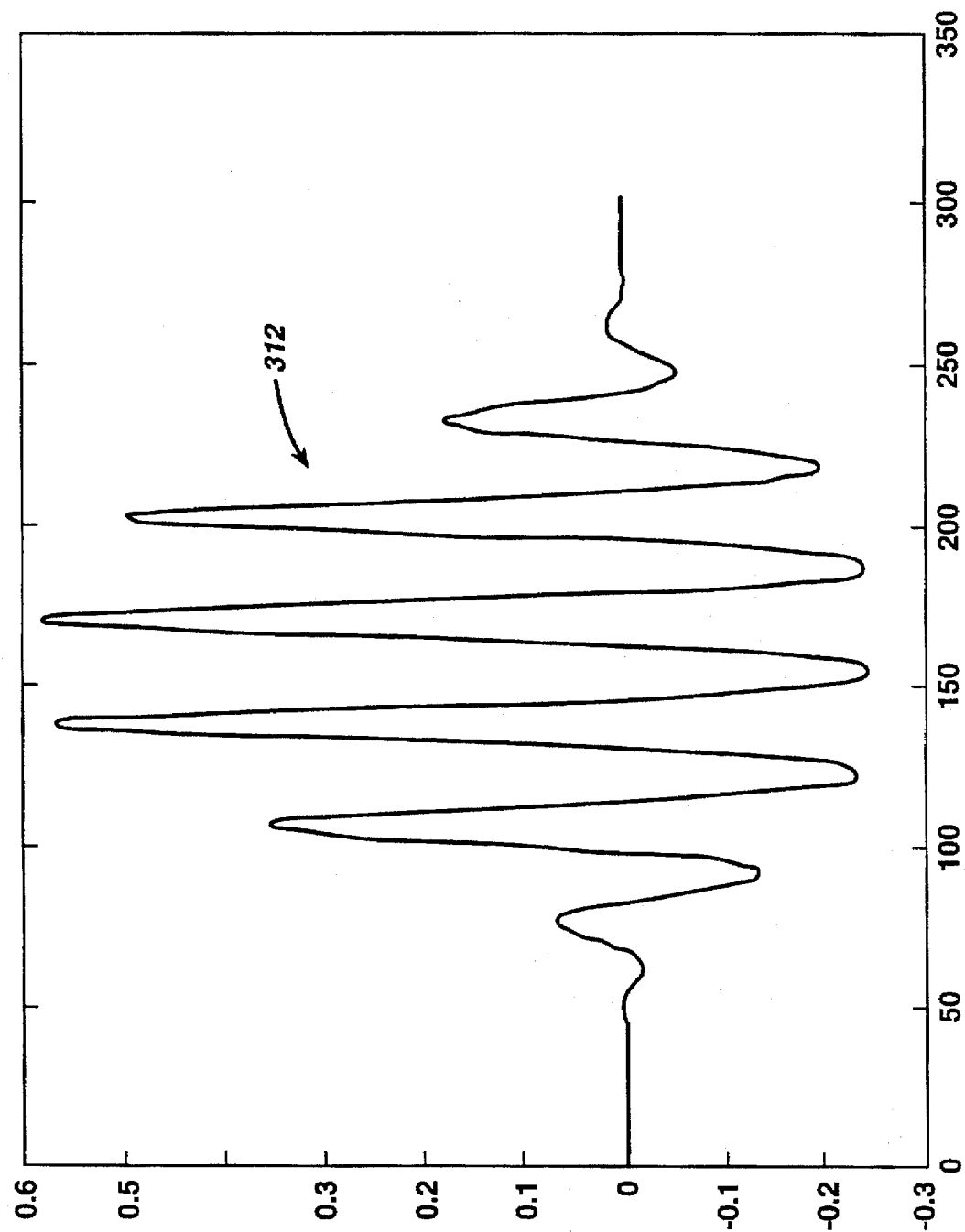

The echoes received from microbubbles in response to these alternate polarity transmissions are shown in FIGS. 5a and 5b. FIG. 5a illustrates an echo waveform 310 received from the first pulsing of a microbubble contrast agent. The nonuniform amplitudes on either side of the zero reference level illustrate nonlinear reflexive action of microbubbles in the presence of acoustic waves, as the microbubbles nonlinearly compress and expand. The echo waveform of 310 FIG. 5a results from transmission of an ultrasonic pulse exhibiting a first polarity.

Figure 5C:
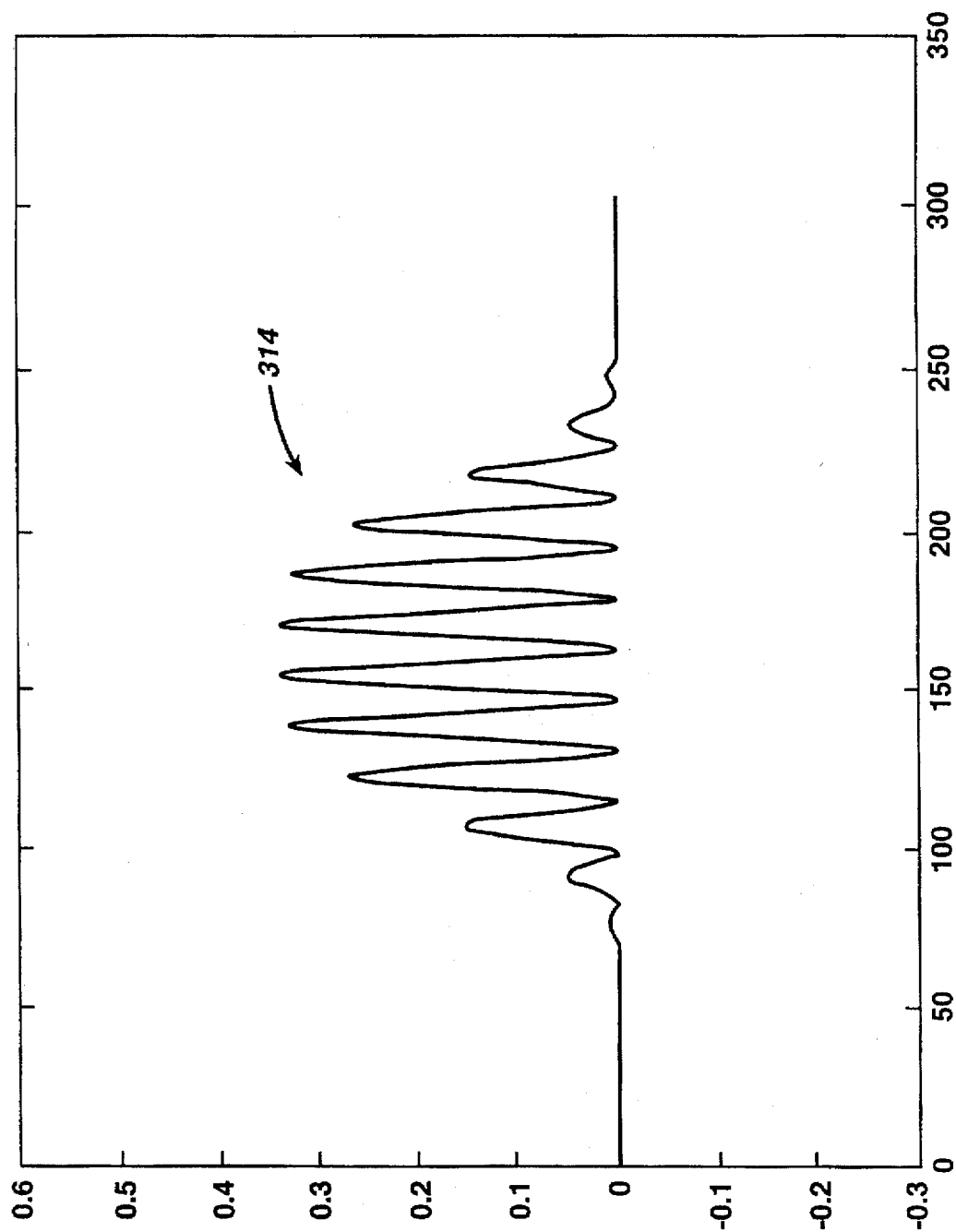

Following transmission of the ultrasonic pulse exhibiting the opposite polarity, the echo waveform 312 of FIG. 5b results. This waveform is similarly nonlinear, but out of phase with the first waveform due to the change in pulse polarity. When the two waveforms are combined, a harmonic response is obtained, as shown in FIG. 5c. The highly nonlinear waveform of FIG. 5c is readily detected, causing the system to become highly sensitive to the contrast agent which produced the nonlinear echo responses.

A mathematical analysis of this effect and response is as follows. To detect the harmonic response of microbubbles, the harmonic component in the incident pressure wave must be suppressed. Based on the analytical solution of the dynamic motion of microbubbles, the primary component of the backscattering pressure magnitude is linearly proportional to the incident pressure and the harmonic component is quadratically proportional to the incident pressure $p_i$ or $p_s(\omega)\alpha p_i$ and $p_s(2\omega)\alpha p_i^2$. Thus, neglecting the higher order terms, one may write the backscattering pressure magnitude $p_B(\omega)$ from a microbubble in a generic form $$P_B(\omega)=k_1(\omega)p+k_2(\omega)p^2 \tag{1}$$

where $k_1$ and $k_2$ are parametrically related to the acoustic properties of the microbubble such as size, viscosity, surface tension, ambient pressure, etc.

Now assume that the microbubble is excited by two narrow band signals at different times but with the same magnitude p and at the same frequency $\omega$, but with opposite polarity: $p_{i1}=p \cos \omega t$ and $p_{i2}=-p \cos \omega t$. Then the backscattered pressure wave from $p_{i1}=p \cos \omega t$ is $$p_{B1}(\omega,t)=k_1(\omega,t)p+k_2(\omega,t)p^2 \tag{2}$$

and from $p_{i2}=-p \cos \omega t$ is $$p_{B2}(\omega,t+\delta t)=k_1(\omega,t+\delta t)p+k_2(\omega,t+\delta t)p^2 \tag{3}$$

Then the total backscattered pressure magnitude may be obtained by summing Equations (2) and (3), $$\begin{aligned} S &= p_{B1}+p_{B2} = (k_1(\omega,t)-k_1(\omega,t+\delta t))p+(k_2(\omega,t)+k_2(\omega,t+\delta t))p^2 \\ &\approx 2k_2(\omega)p^2 \end{aligned} \tag{4}$$

Equation (4) shows that the primary component is eliminated if $k_1(\omega)$ and $k_2(\omega)$ do not change substantially in the time duration $\delta t$, where $\delta t$ is small.

Assume the backscattering from microbubbles is quasi-stationary over T, where T is the pulse repetition interval. Therefore, the average nonlinear acoustic properties are not changed over time T, or $$E\{k_1(\omega,t)\}=E\{k_1(\omega,t+T)\}$$

and $$E\{k_2(\omega t)\}=E\{k_2(\omega,t+T)\}.$$

The relationship of Equation (4) will hold by summing the pulse echoes from two pulses which are time-diverse in T. The quasi-stationary assumption is valid for slow perfused flow, such as myocardial perfusion.

When the bandwidth of the incident pressure wave is wide, the wideband excitation wave P(t) may be represented by a Fourier series $$P(t) = \sum_i A(\omega_i)\cos\omega_i t$$

Thus the backscattered pressure magnitude of the microbubbles from P(t) may be written as $$P_{B1} = \sum_i k_1(\omega_i)A(\omega_i) + \sum_i k_2(\omega_i)A^2(\omega_i) \quad (5)$$

and the backscattered pressure magnitude of the microbubbles from $-P(t)$ may be written as $$P_{B2} = -\sum_i k_1(\omega_i)A(\omega_i) + \sum_i k_2(\omega_i)A^2(\omega_i) \quad (6)$$

Summing Equations (5) and (6), one may obtain $$S = p_{B1} + p_{B2} = 2\sum_i k_2(\omega_i)A^2(\omega_i) \quad (7)$$

Again, the harmonic component is extracted and the primary component is eliminated.

Let us assume the nonlinearity in tissue is negligible. Since the backscattered pressure in a linear medium is linearly proportional to the incident pressure wave, the polarity of the backscattered wave will be changed as the polarity of the incident pressure wave is changed. Assuming the tissue is relatively stationary during the period of two consecutive pulses, summing the pulse echoes from consecutive pulses with opposite polarity will cancel the echo response from tissue. Thus, tissue clutter will be suppressed.

The concept of summing the pulse echoes from two pulses of opposite polarity may be generalized into processing echoes from multiple pulses with alternate polarity to maximize the sensitivity and minimize the variance, assuming the tissue is stationary during the pulsing interval. Let the pulse sequence be $$P = \{p \; -p \; p \; -p \; p \; -p \; \cdots \; -p \; p\}$$

and the pulse echoes be $$E = \{E_1 \; E_2 \; E_3 \; E_4 \; E_5 \; E_6 \cdots E_n\}$$

Accumulating the partial sum of consecutive pairs of echoes results in $$S = \sum_{j=1}^{n-1} E_j + E_{j+1} = 2(n-1)\sum_i k_2(\omega_i)A^2(\omega_i)$$

What is claimed is:

1. A method of ultrasonically detecting the ultrasonic response of an ultrasonic contrast agent comprising the steps of:

transmitting a first ultrasonic pulse to said ultrasonic contrast agent to cause a first harmonic response;

transmitting a second ultrasonic pulse of a different polarity than said first ultrasonic pulse to said harmonic contrast agent to cause a second harmonic response;

detecting said first and second harmonic responses; and combining said first and second harmonic responses.

2. The method of claim 1, wherein said step of combining comprises summing said first and second harmonic responses.

3. The method of claim 1, wherein said step of combining comprises integrating said first and second harmonic responses.

4. The method of claim 1, wherein said transmitting step comprises transmitting pulses which exhibit a pulse energy which is within a range which causes microbubbles of said ultrasonic contrast agent to oscillate without substantial microbubble destruction.

\* \* \* \* \*

UNITED STATES PATENT AND TRADEMARK OFFICE
CERTIFICATE OF CORRECTION

PATENT NO. : 5,706,819　　　　　　　　　　　　　　　　Page 1 of 2
DATED : January 13, 1998
INVENTOR(S) : Juin-Jet Hwang, et al.

It is certified that error appears in the above-identified patent and that said Letters Patent is hereby corrected as shown below:

Title page, insert the following:

--Related U.S. Application Data
[60] Provisional application No.60/005,009 filed October 10, 1995.--

Column 1, line 2, insert the following:

--CROSS REFFERENCE TO RELATED APPLICATION
Reference is made to and priority claimed from U.S. Provisional application Ser. No.
US 60/005,009, filed October 10, 1995, entitled PERFUSION MEASUREMENT USING CONTRAST AGENTS--

UNITED STATES PATENT AND TRADEMARK OFFICE
CERTIFICATE OF CORRECTION

PATENT NO. : 5,706,819
DATED : January 13, 1998
INVENTOR(S) : Juin-Jet Hwang and David Hope-Simpson It is certified that error appears in the above-identified patent and that said Letters Patent is hereby corrected as shown below:

In col. 1, line 3 immediately following the title, insert

--This application claims the benefit of U. S. Provisional Application No. 60/005,009, filed October 10, 1995.--

Signed and Sealed this

Second Day of March, 1999

Attest:

Attesting Officer

Q. TODD DICKINSON

Acting Commissioner of Patents and Trademarks